(12) United States Patent
Sartor

(10) Patent No.: US 8,004,121 B2
(45) Date of Patent: *Aug. 23, 2011

(54) CONNECTION CABLE AND METHOD FOR ACTIVATING A VOLTAGE-CONTROLLED GENERATOR

(75) Inventor: Joe D. Sartor, Longmont, CO (US)

(73) Assignee: TYCO Healthcare Group LP, Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/902,287

(22) Filed: Oct. 12, 2010

(65) Prior Publication Data

US 2011/0028969 A1 Feb. 3, 2011

Related U.S. Application Data

(62) Division of application No. 11/879,180, filed on Jul. 16, 2007, now Pat. No. 7,834,484.

(51) Int. Cl.
*A61B 18/00* (2006.01)
(52) U.S. Cl. ......... 307/116; 307/147; 307/125; 307/130
(58) Field of Classification Search .................. 307/116, 307/125, 130, 147
See application file for complete search history.

(56) References Cited

U.S. PATENT DOCUMENTS

| | | | |
|---|---|---|---|
| 3,154,365 A | 10/1964 | Crimmins | |
| 3,768,019 A | 10/1973 | Podowski | |
| 3,898,554 A | 8/1975 | Knudsen | |
| 4,296,413 A | 10/1981 | Milkovic | |
| 4,595,248 A | 6/1986 | Brown | |
| 4,727,874 A | 3/1988 | Bowers et al. | |
| 4,767,999 A | 8/1988 | VerPlanck | |
| 4,768,969 A | 9/1988 | Bauer et al. | |
| 4,827,927 A | 5/1989 | Newton | |
| 4,862,889 A | 9/1989 | Feucht | |

(Continued)

FOREIGN PATENT DOCUMENTS

EP 1707144 3/2006

(Continued)

OTHER PUBLICATIONS

Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.

(Continued)

*Primary Examiner* — Fritz M Fleming

(57) ABSTRACT

A connection cable is disclosed for controlling a voltage-controlled generator such as an electrosurgery generator from a controlling device such as a robotic surgery system. The cable includes a first connector adapted to connect to a voltage-controlled generator and a second connector adapted to connect to a controlling device. Within the cable is a voltage divider interdisposed between the first connector and the second connector. The voltage divider is configured to divide a reference voltage provided by the voltage-controlled generator into at least one control voltage which is selectable by the controlling device. The cable additionally includes a plurality of electrical wires which operatively connect the first connector, the second connector and the voltage divider. During robotic electrosurgery, said operating parameters can be actuated by a surgeon operating at the robotic surgical system console, which causes a corresponding control voltage to be switched to a control voltage input on an electrosurgery generator, which, in turn, generates a corresponding electrosurgical signal in response thereto.

14 Claims, 5 Drawing Sheets

U.S. PATENT DOCUMENTS

| | | | |
|---|---|---|---|
| 5,044,977 A | 9/1991 | Vindigni | |
| 5,067,953 A | 11/1991 | Feucht | |
| 5,075,839 A | 12/1991 | Fisher et al. | |
| 5,119,284 A | 6/1992 | Fisher et al. | |
| 5,161,893 A | 11/1992 | Shigezawa et al. | |
| 5,167,659 A | 12/1992 | Ohtomo et al. | |
| 5,234,427 A | 8/1993 | Ohtomo et al. | |
| 5,249,585 A | 10/1993 | Turner et al. | |
| 5,282,840 A | 2/1994 | Hudrlik | |
| 5,290,283 A | 3/1994 | Suda | |
| 5,295,857 A | 3/1994 | Toly | |
| 5,304,917 A | 4/1994 | Somerville | |
| 5,342,356 A * | 8/1994 | Ellman et al. | 606/32 |
| 5,346,406 A | 9/1994 | Hoffman et al. | |
| 5,346,491 A | 9/1994 | Oertli | |
| 5,422,926 A | 6/1995 | Smith et al. | |
| 5,423,811 A | 6/1995 | Imran et al. | |
| 5,429,596 A | 7/1995 | Arias et al. | |
| 5,452,725 A | 9/1995 | Martenson | |
| 5,454,809 A | 10/1995 | Janssen | |
| 5,474,464 A | 12/1995 | Drewnicki | |
| 5,496,314 A | 3/1996 | Eggers | |
| 5,511,993 A | 4/1996 | Yamada et al. | |
| 5,540,677 A | 7/1996 | Sinofsky | |
| 5,540,682 A | 7/1996 | Gardner et al. | |
| 5,541,376 A | 7/1996 | Ladtkow et al. | |
| 5,545,161 A | 8/1996 | Imran | |
| 5,562,720 A | 10/1996 | Stern et al. | |
| 5,609,560 A | 3/1997 | Ichikawa et al. | |
| 5,620,481 A | 4/1997 | Desai et al. | |
| 5,628,771 A | 5/1997 | Mizukawa et al. | |
| 5,664,953 A | 9/1997 | Reylek | |
| 5,678,568 A | 10/1997 | Uchikubo et al. | |
| 5,681,307 A | 10/1997 | McMahan | |
| 5,693,078 A | 12/1997 | Desai et al. | |
| 5,697,925 A | 12/1997 | Taylor | |
| 5,697,927 A | 12/1997 | Imran et al. | |
| 5,720,742 A | 2/1998 | Zacharias | |
| 5,735,846 A | 4/1998 | Panescu et al. | |
| 5,738,683 A | 4/1998 | Osypka | |
| 5,743,900 A | 4/1998 | Hara | |
| 5,743,903 A | 4/1998 | Stern et al. | |
| 5,766,153 A | 6/1998 | Eggers et al. | |
| 5,788,688 A | 8/1998 | Bauer et al. | |
| 5,807,253 A | 9/1998 | Dumoulin et al. | |
| 5,810,804 A | 9/1998 | Gough et al. | |
| 5,817,091 A | 10/1998 | Nardella et al. | |
| 5,843,019 A | 12/1998 | Eggers et al. | |
| 5,843,075 A | 12/1998 | Taylor | |
| 5,849,010 A | 12/1998 | Wurzer et al. | |
| 5,853,409 A | 12/1998 | Swanson et al. | |
| 5,860,832 A | 1/1999 | Wayt et al. | |
| 5,865,788 A | 2/1999 | Edwards et al. | |
| 5,891,142 A | 4/1999 | Eggers et al. | |
| 5,906,614 A | 5/1999 | Stern et al. | |
| 5,944,553 A | 8/1999 | Yasui et al. | |
| 5,957,961 A | 9/1999 | Maguire et al. | |
| 5,959,253 A | 9/1999 | Shinchi | |
| 5,964,746 A | 10/1999 | McCary | |
| 5,971,981 A | 10/1999 | Hill et al. | |
| 6,007,532 A | 12/1999 | Netherly | |
| 6,013,074 A | 1/2000 | Taylor | |
| 6,017,338 A | 1/2000 | Brucker et al. | |
| 6,017,354 A | 1/2000 | Culp et al. | |
| 6,022,346 A | 2/2000 | Panescu et al. | |
| 6,022,347 A | 2/2000 | Lindenmeier et al. | |
| 6,039,731 A | 3/2000 | Taylor et al. | |
| 6,039,732 A | 3/2000 | Ichikawa et al. | |
| 6,041,260 A | 3/2000 | Stern et al. | |
| 6,059,781 A | 5/2000 | Yamanashi et al. | |
| 6,066,137 A | 5/2000 | Greep | |
| 6,074,089 A | 6/2000 | Hollander et al. | |
| 6,088,614 A | 7/2000 | Swanson | |
| 6,102,907 A | 8/2000 | Smethers et al. | |
| 6,113,592 A | 9/2000 | Taylor | |
| 6,113,593 A | 9/2000 | Tu et al. | |
| 6,123,701 A | 9/2000 | Nezhat | |
| 6,162,184 A | 12/2000 | Swanson et al. | |
| 6,165,169 A | 12/2000 | Panescu et al. | |
| 6,183,468 B1 | 2/2001 | Swanson et al. | |
| 6,186,147 B1 | 2/2001 | Cobb | |
| 6,193,713 B1 | 2/2001 | Geistert et al. | |
| 6,197,023 B1 | 3/2001 | Muntermann | |
| 6,216,704 B1 | 4/2001 | Ingle et al. | |
| 6,228,078 B1 | 5/2001 | Eggers et al. | |
| 6,232,556 B1 | 5/2001 | Daugherty et al. | |
| 6,235,022 B1 | 5/2001 | Hallock et al. | |
| 6,237,604 B1 | 5/2001 | Burnside et al. | |
| 6,241,723 B1 | 6/2001 | Heim et al. | |
| 6,243,654 B1 | 6/2001 | Johnson et al. | |
| 6,245,061 B1 | 6/2001 | Panescu et al. | |
| 6,245,063 B1 | 6/2001 | Uphoff | |
| 6,254,422 B1 | 7/2001 | Feye-Hohmann | |
| 6,267,760 B1 | 7/2001 | Swanson | |
| 6,293,943 B1 | 9/2001 | Panescu et al. | |
| 6,322,558 B1 | 11/2001 | Taylor et al. | |
| 6,371,963 B1 | 4/2002 | Nishtala et al. | |
| 6,402,742 B1 | 6/2002 | Blewett et al. | |
| 6,402,748 B1 | 6/2002 | Schoenman et al. | |
| 6,409,722 B1 | 6/2002 | Hoey et al. | |
| 6,413,256 B1 | 7/2002 | Truckai et al. | |
| 6,422,896 B2 | 7/2002 | Aoki et al. | |
| 6,423,057 B1 | 7/2002 | He et al. | |
| 6,426,886 B1 | 7/2002 | Goder | |
| 6,428,537 B1 | 8/2002 | Swanson et al. | |
| 6,440,157 B1 | 8/2002 | Shigezawa et al. | |
| 6,454,594 B2 | 9/2002 | Sawayanagi | |
| 6,458,122 B1 | 10/2002 | Pozzato | |
| 6,468,270 B1 | 10/2002 | Hovda et al. | |
| 6,468,273 B1 | 10/2002 | Leveen et al. | |
| 6,482,201 B1 | 11/2002 | Olsen et al. | |
| 6,488,678 B2 | 12/2002 | Sherman | |
| 6,494,880 B1 | 12/2002 | Swanson et al. | |
| 6,497,659 B1 | 12/2002 | Rafert | |
| 6,522,931 B2 | 2/2003 | Manker et al. | |
| 6,537,272 B2 | 3/2003 | Christopherson et al. | |
| 6,544,260 B1 | 4/2003 | Markel et al. | |
| 6,546,270 B1 | 4/2003 | Goldin et al. | |
| 6,557,559 B1 | 5/2003 | Eggers et al. | |
| 6,558,377 B2 | 5/2003 | Lee et al. | |
| 6,565,562 B1 | 5/2003 | Shah et al. | |
| 6,578,579 B2 | 6/2003 | Burnside et al. | |
| 6,579,288 B1 | 6/2003 | Swanson et al. | |
| 6,602,243 B2 | 8/2003 | Noda | |
| 6,602,252 B2 | 8/2003 | Mollenauer | |
| 6,611,793 B1 | 8/2003 | Burnside et al. | |
| 6,620,189 B1 | 9/2003 | Machold et al. | |
| 6,626,901 B1 | 9/2003 | Treat et al. | |
| 6,632,193 B1 | 10/2003 | Davison et al. | |
| 6,635,056 B2 | 10/2003 | Kadhiresan et al. | |
| 6,651,669 B1 | 11/2003 | Burnside | |
| 6,652,513 B2 | 11/2003 | Panescu et al. | |
| 6,653,569 B1 | 11/2003 | Sung | |
| 6,656,177 B2 | 12/2003 | Truckai et al. | |
| 6,663,627 B2 | 12/2003 | Francischelli et al. | |
| 6,672,151 B1 | 1/2004 | Schultz et al. | |
| 6,695,837 B2 * | 2/2004 | Howell | 606/29 |
| 6,696,844 B2 | 2/2004 | Wong et al. | |
| 6,730,078 B2 | 5/2004 | Simpson et al. | |
| 6,730,079 B2 | 5/2004 | Lovewell | |
| 6,743,225 B2 | 6/2004 | Sanchez et al. | |
| 6,746,284 B1 | 6/2004 | Spink, Jr. | |
| 6,749,624 B2 | 6/2004 | Knowlton | |
| 6,761,716 B2 | 7/2004 | Kadhiresan et al. | |
| 6,784,405 B2 | 8/2004 | Flugstad et al. | |
| 6,792,390 B1 | 9/2004 | Burnside et al. | |
| 6,796,980 B2 | 9/2004 | Hall | |
| 6,809,508 B2 | 10/2004 | Donofrio | |
| 6,818,000 B2 | 11/2004 | Muller et al. | |
| 6,837,888 B2 | 1/2005 | Ciarrocca et al. | |
| 6,843,682 B2 | 1/2005 | Matsuda et al. | |
| 6,890,331 B2 | 5/2005 | Kristensen | |
| 6,899,538 B2 | 5/2005 | Matoba | |
| 6,936,047 B2 | 8/2005 | Nasab et al. | |
| 6,939,344 B2 | 9/2005 | Kreindel | |
| 6,958,064 B2 | 10/2005 | Rioux et al. | |
| 6,962,587 B2 | 11/2005 | Johnson et al. | |

| | | |
|---|---|---|
| 6,974,453 B2 | 12/2005 | Woloszko et al. |
| 6,974,463 B2 | 12/2005 | Magers et al. |
| 6,977,495 B2 | 12/2005 | Donofrio |
| 6,984,231 B2 | 1/2006 | Goble et al. |
| 7,001,379 B2 | 2/2006 | Behl et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,074,217 B2 | 7/2006 | Strul et al. |
| 7,083,618 B2 | 8/2006 | Couture et al. |
| 7,094,231 B1 | 8/2006 | Ellman et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |
| 7,131,445 B2 | 11/2006 | Amoah |
| 7,146,210 B2 | 12/2006 | Palti |
| 7,151,964 B2 | 12/2006 | Desai et al. |
| 7,153,300 B2 | 12/2006 | Goble |
| 7,156,842 B2 | 1/2007 | Sartor et al. |
| 7,156,844 B2 | 1/2007 | Reschke et al. |
| 7,156,846 B2 | 1/2007 | Dycus et al. |
| 7,163,536 B2 | 1/2007 | Godara |
| 7,169,144 B2 | 1/2007 | Hoey et al. |
| 7,192,427 B2 | 3/2007 | Chapelon et al. |
| 7,195,627 B2 | 3/2007 | Amoah et al. |
| 7,203,556 B2 | 4/2007 | Daners |
| 7,217,269 B2 | 5/2007 | El-Galley et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,238,181 B2 | 7/2007 | Daners et al. |
| 7,238,183 B2 | 7/2007 | Kreindel |
| 7,244,255 B2 | 7/2007 | Daners et al. |
| 7,250,048 B2 | 7/2007 | Francischelli et al. |
| 7,258,688 B1 | 8/2007 | Shah et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,437 B2 | 11/2007 | Pozzato |
| 7,305,311 B2 | 12/2007 | Van Zyl |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,578 B2 | 4/2008 | Francischelli et al. |
| 7,364,972 B2 | 4/2008 | Ono et al. |
| 7,402,754 B2 | 7/2008 | Kirwan, Jr. et al. |
| D574,323 S | 8/2008 | Waaler |
| 7,407,502 B2 | 8/2008 | Strul et al. |
| 7,416,437 B2 | 8/2008 | Sartor et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,470,272 B2 | 12/2008 | Mulier et al. |
| 7,477,080 B1 | 1/2009 | Fest |
| 7,479,140 B2 | 1/2009 | Ellman et al. |
| 7,491,199 B2 | 2/2009 | Goble |
| 7,491,201 B2 | 2/2009 | Shields et al. |
| 7,513,896 B2 | 4/2009 | Orszulak |
| 7,525,398 B2 | 4/2009 | Nishimura et al. |
| 2004/0030330 A1 | 2/2004 | Brassell et al. |
| 2004/0172016 A1 | 9/2004 | Bek et al. |
| 2005/0004634 A1 | 1/2005 | Ricart et al. |
| 2005/0109111 A1 | 5/2005 | Manlove et al. |
| 2005/0131390 A1* | 6/2005 | Heinrich et al. .................. 606/1 |
| 2006/0111711 A1 | 5/2006 | Goble |
| 2006/0281360 A1 | 12/2006 | Sartor et al. |
| 2006/0291178 A1 | 12/2006 | Shih |
| 2007/0173810 A1 | 7/2007 | Orszulak |
| 2008/0015563 A1 | 1/2008 | Hoey et al. |
| 2008/0177199 A1 | 7/2008 | Podhajsky |
| 2008/0248685 A1 | 10/2008 | Sartor et al. |
| 2008/0281315 A1 | 11/2008 | Gines |
| 2008/0281316 A1 | 11/2008 | Carlton et al. |
| 2008/0287791 A1 | 11/2008 | Orszulak et al. |
| 2008/0287838 A1 | 11/2008 | Orszulak et al. |
| 2009/0018536 A1 | 1/2009 | Behnke |
| 2009/0024120 A1 | 1/2009 | Sartor |
| 2009/0036883 A1 | 2/2009 | Behnke |
| 2009/0069801 A1 | 3/2009 | Jensen et al. |
| 2009/0082765 A1 | 3/2009 | Collins et al. |
| 2009/0157071 A1 | 6/2009 | Wham et al. |
| 2009/0157072 A1 | 6/2009 | Wham et al. |
| 2009/0157073 A1 | 6/2009 | Orszulak |
| 2009/0157075 A1 | 6/2009 | Wham et al. |

FOREIGN PATENT DOCUMENTS

| | | |
|---|---|---|
| EP | 1744354 | 1/2007 |
| EP | 1854423 | 11/2007 |
| FR | 2364461 | 7/1978 |
| GB | 702510 | 1/1954 |
| WO | WO95/25471 | 9/1995 |
| WO | WO98/07378 | 2/1998 |
| WO | WO98/18395 | 5/1998 |
| WO | WO98/27880 | 7/1998 |
| WO | WO99/12607 | 3/1999 |
| WO | WO02/00129 | 1/2002 |
| WO | WO2004/043240 | 5/2004 |
| WO | WO2004/052182 | 6/2004 |
| WO | WO2006/050888 | 5/2006 |
| WO | WO2006/105121 | 10/2006 |

OTHER PUBLICATIONS

International Search Report EP04707738 dated Jul. 4, 2007.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report PCT/US03/33711 dated Jul. 16, 2004.
International Search Report PCT/US03/33832 dated Jun. 17, 2004.
International Search Report PCT/US04/02961 dated Aug. 2, 2005.
US 6,878,148, 04/2005, Goble et al. (withdrawn)

* cited by examiner

CONNECTION CABLE AND METHOD FOR ACTIVATING A VOLTAGE-CONTROLLED GENERATOR

CROSS-REFERENCE TO RELATED APPLICATION

This application is a divisional of U.S. application Ser. No. 11/879,180, filed Jul. 16, 2007, now U.S. Pat. No. 7,834,484 the entirety of which is hereby incorporated by reference herein for all purposes.

BACKGROUND

1. Technical Field

The present disclosure relates generally to the field of minimally invasive surgery performed using electrosurgical techniques, and in particular, to a connection cable and method for connecting an electrosurgery generator to a robotic surgery system, enabling the electrosurgical generator to be controlled by a surgeon at the robotic master console.

2. Background of Related Art

Electrosurgery is a technique of using alternating current electrical signals, using a carrier frequency in the approximately 200 kHz-3.3 mHz range, in connection with surgical instruments, to cut or coagulate biologic tissue endogenically. This electrosurgical signal can be a sinusoidal waveform operating in a continuous mode at a 100% duty cycle, or pulse modulated at a duty cycle of less than 100%. Typically, electrosurgical signals are operated at 100% duty cycle for maximal cutting effect, and are pulse modulated at duty cycles ranging from 50% to 25% for less aggressive cutting, also referred to as blending, or, at a substantially lower duty cycle of approximately 6%, for coagulating. The electrosurgical carrier signal can also be varied in intensity. The electrosurgical signal is applied to the patient via electrodes in either monopolar mode, or bipolar mode. In monopolar mode, the active electrode is the surgical instrument at the surgical site, and the return electrode is elsewhere on the patient, such that the electrosurgical signal passes through the patient's body from the surgical site to the return electrode. In bipolar mode, both the active and return electrodes are at the surgical site, effectuated by, for example, both tines of a pair of forceps, such that the electrosurgical signal passes through only the tissue that is held between the tines of the instrument. A surgeon's decision to use monopolar or bipolar mode electrosurgery is often based upon various factors, including for example the type of procedure to be performed, or whether the patient is fitted with a metallic prosthesis or cardiac pacemaker.

A surgeon performs robotic surgery by sitting at a robotic master console and viewing a three-dimensional virtual operative field, while manipulating controls that remotely control robotic arms mounted on a separate robotic surgical cart. The robotic arms hold surgical instruments that follow the surgeon's hand motions, and a stereoscopic video camera that transmits a three-dimensional view of the operative field to the surgeon. The three-dimensional imaging, the hand-like motions of the robotic instruments, and the ability to assist the surgeon through motion scaling and tremor reduction techniques facilitate advanced minimally-invasive procedures that could not otherwise be performed using traditional endoscopic techniques.

When performing electrosurgery with manual (non-robotic) instruments, a surgeon can actuate an electrosurgery generator using hand switches located on the surgical instrument. For example, the surgeon can selectively apply a cutting waveform, a blending waveform or a coagulating waveform using the hand controls. However, this is not desirable or practical in the case of robotic surgery, because the surgical instruments are remotely controlled by a surgeon who is operating a robotic master console, which is located away from the patient.

The use of existing electrosurgery generators with robotic surgery systems without the need to modify or upgrade existing electrosurgery generators would be a great achievement in electrosurgery and may ultimately achieve interoperability with robotic surgery systems and minimize or eliminate training and certification requirements imposed on physicians and other medical facility staff arising from the deployment of such modified electrosurgery generators.

SUMMARY

It is an aspect of the present disclosure to provide a connection cable for actuating a voltage-controlled generator from a controlling device. Control signals originating within a controlling device are adapted for use by the voltage-controlled generator by an interface provided within the cable. In an embodiment, the cable has a first end, which includes a first connector adapted to connect to a voltage-controlled generator, such as an electrosurgery generator; a second end, which includes a second connector adapted to connect to a controlling device, such as a remotely-controlled robotic surgery system. A voltage divider is interdisposed between the first connector and the second connector, the voltage divider being configured to divide a reference voltage provided by the electrosurgery generator into at least one control voltage for selection by the controlling device. Each control voltage corresponds to an operating mode, command or parameter related to the electrosurgery generator, for example, a cut operation, a blend operation, and a coagulate operation. The connection cable includes a plurality of electrical conductors which operatively connect the first connector, the second connector, and the voltage divider.

Control signals in the form of at least one switch closure, each corresponding to a desired operating mode of the electrosurgery generator, originate within the robotic surgery system. The switch closure completes an electrical circuit whereby a corresponding control voltage is routed from the voltage divider to a mode input of the electrosurgery generator, which, in turn, generates the desired electrosurgery signal.

In an embodiment of the present disclosure, the voltage dividing network is disposed between +5 volts dc (+5Vdc) and ground (0Vdc) and is configured to provide at least one control voltage corresponding to an operating mode of the electrosurgery generator. In an embodiment, the voltage divider is comprised of four resistors connected in series, which, continuing with the present example, provides, in addition to the reference voltages of 0Vdc and +5.0Vdc, three voltage taps, making available at each tap a control voltage corresponding to an operating mode of the electrosurgical generator, for example, a cutting, blending and coagulating mode. Each voltage tap is operably connected to a first contact of a switch configured for switching the voltage tap to the mode input of an electrosurgery generator.

In an embodiment, the switch includes a normally-open single pole single throw (SPST) switch within the robotic master console for actuation by a surgeon. It is also envisioned that the at least one switch can be a set of relay contacts, a solid-state switch, or inductive, capacitive, or other switching means as now or in the future may be known, capable of actuation by a surgeon operating the robotic surgery console and/or by the operational software of the robotic surgery system. A contact of each SPST switch is commonly and operably connected to a control input, also known as a mode input, of the electrosurgery generator configured to sense the presence of a control voltage and to produce a corresponding electrosurgical signal in response thereto. When the at least one SPST switch is closed, an electrical circuit is completed whereby a control voltage is applied to the mode input of an electrosurgery generator, which causes a corresponding electrosurgical signal to be produced in accordance with the present disclosure.

In addition to control signals disclosed herein, the present disclosure contemplates that the generated electrosurgery signal be transmitted from the electrosurgery generator to the surgical instrument, or to the robotic surgery system, by a transmission wire within the connection cable herein described.

Also envisioned is a connection cable capable of interfacing a plurality of electrosurgery generators to a single controlling device, such as a robotic surgery system. Such plurality of electrosurgery generators can be of a type which are collectively housed in a single chassis or operating unit, or housed separately in individual chassis. Such plurality of electrosurgery generators can share a common control port whereby a single connection from the robotic surgical system is capable of controlling said plurality of electrosurgery generators.

The present disclosure further provides for a connection cable adapted for use with an existing hand switch interface port on an electrosurgery generator. The hand switch interface port is typically situated on the front panel of an electrosurgery generator thereby enabling the switch interface to be used with a robotic surgery system without requiring hardware or software modifications to known electrosurgery generators which are in popular use.

A method for interfacing an electrosurgery generator to a robotic surgery system is also disclosed wherein at least one control signal originating within a robotic surgery system is adapted for use by the electrosurgery generator by an interface provided within the cable. The method further includes the steps of: providing a voltage-controlled electrosurgery generator and a robotic surgery system electrically coupled thereto; dividing a reference voltage provided by the voltage-controlled generator into at least one control voltage; interfacing control signals originating within the robotic surgery system or other controlling system to the electrosurgery generator via a connector adapted for connecting to the robotic surgery system; selecting an at least one control voltage in accordance with a control signal originating within the robotic surgery system; and applying the control voltage to a control input of an electrosurgery generator adapted to sense the presence of said control voltage and to produce a corresponding electrosurgical signal in response thereto.

It is envisioned that the steps of the method in accordance with the present disclosure can be performed in a different ordering than the ordering provided herein.

The present disclosure further contemplates an apparatus for performing robotic electrosurgery comprising an electrosurgery generator configured to accept a control voltage at a control voltage input and to produce a corresponding electrosurgical signal in response thereto. A surgeon, from the robotic master console, can cause to be activated a control signal corresponding to an electrosurgery signal. An interface may be configured to convert the control signal into a control voltage and to apply the control voltage to the control voltage input of the electrosurgery generator, thereby causing an electrosurgery signal to be generated. In an embodiment, the interface includes a voltage divider for providing at least one control voltage for application to the control voltage input of the electrosurgery generator via at least one switch. Optionally, the interface is additionally configured to transmit the electrosurgical signal to a surgical instrument of the robotic surgical system.

BRIEF DESCRIPTION OF THE DRAWINGS

Various embodiments of the present disclosure will be described herein below with reference to the figures wherein.

DETAILED DESCRIPTION

Figure 1A:
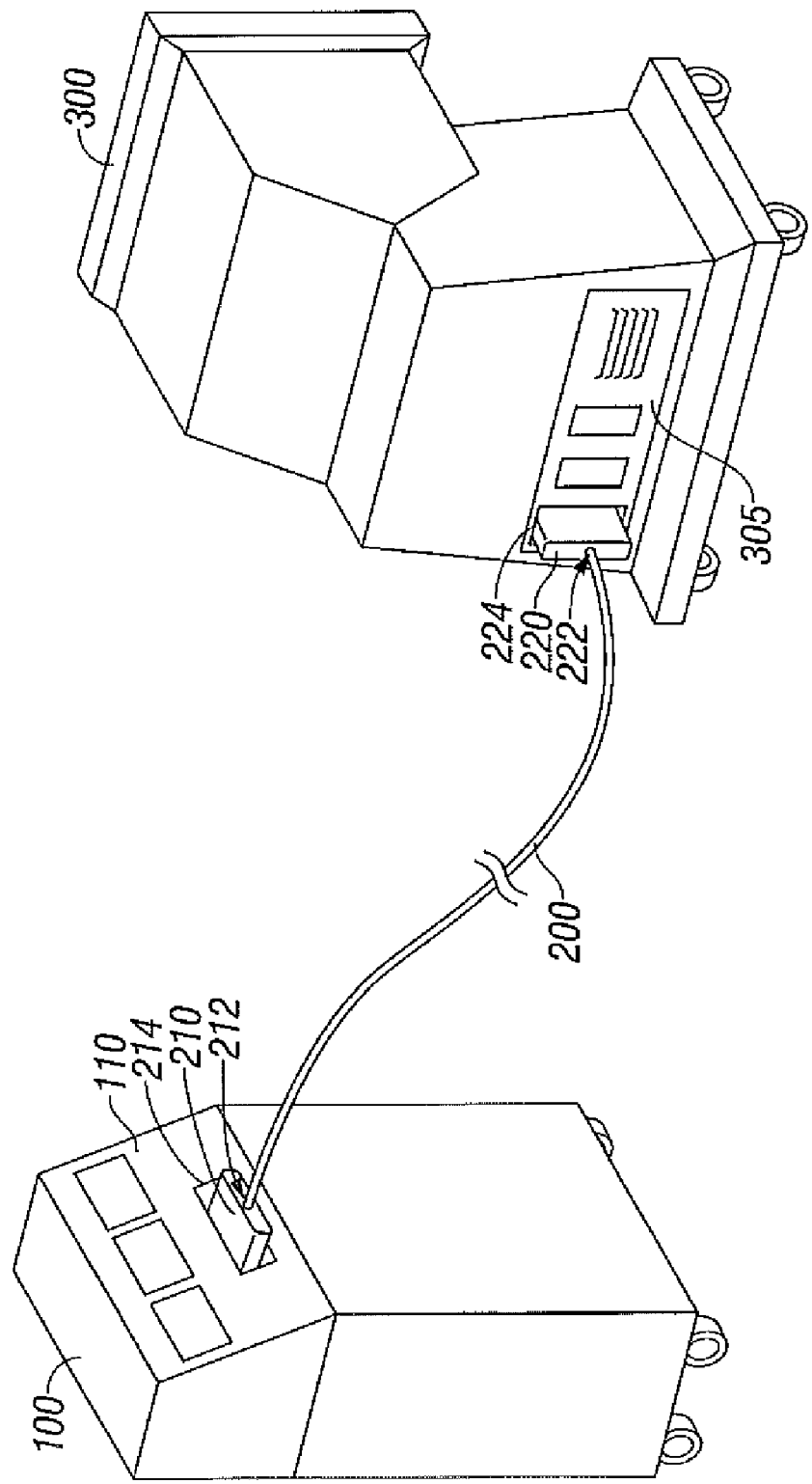
FIG. 1A is a schematic of an electrosurgery generator coupled to a robotic surgery system master console according to an embodiment of the present disclosure.

Embodiments of the presently disclosed connection cable are described herein in detail with reference to the drawings, in which like reference numerals designate identical or corresponding elements in each of the several views.

The present disclosure provides a connection cable for connecting an electrosurgery generator to a robotic surgical system enabling the electrosurgical generator to be controlled by a surgeon at the robotic master console.

Figure 1B:
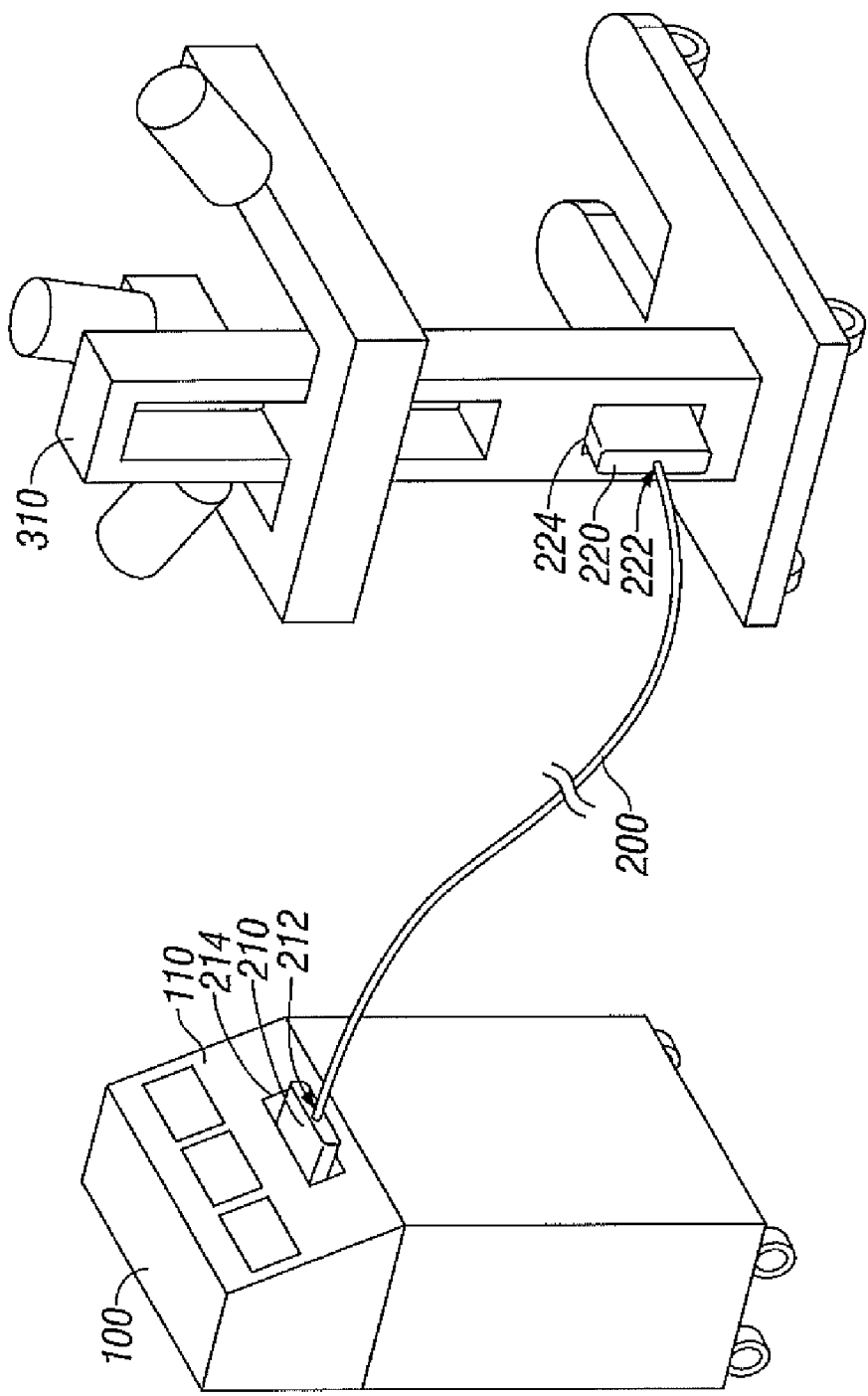
FIG. 1B is a schematic of an electrosurgery generator coupled to a robotic surgery system robotic arm cart according to an embodiment of the present disclosure.

Referring to FIG. 1A, there is disclosed a connection cable 200 having an electrosurgery generator end 212 and a robotic surgical system end 222 for coupling an electrosurgery generator 100 to a robotic surgical system master console 300. Additionally or alternatively, electrosurgery generator 100 can also be coupled by connection cable 200 to a robotic surgical system surgical arm cart 310, as illustrated in FIG. 1B, and/or to other modules (not shown) of the robotic surgical system. Connection cable 200 is detachably coupled at the electrosurgery generator end 212 to electrosurgery generator 100 by connector 210 to a corresponding mating connector 214 provided on electrosurgery generator 100, typically located at, but not limited to, front panel 110 of electrosurgery generator 100.

Connection cable 200 is detachably coupled at robotic surgical system end 222 by connector 220 to a corresponding mating connector 224 provided on at least one of a robotic surgical system master console 300 and located typically on an interface panel 305, a robotic surgical system surgical arm cart 310, or an additional or alternative connector (not shown) provided by the robotic surgical system.

In use, a surgeon or operating room assistant can quickly configure an electrosurgery generator and a robotic surgery system into a robotic electrosurgery arrangement by engaging connector 210 to corresponding mating connector 214 and by engaging connector 220 to its corresponding mating connector 224 or to corresponding mating connector 224 at robotic surgery system surgical arm cart 310, or to a corresponding mating connector (not shown) provided elsewhere at the robotic surgical system.

Figure 2A:
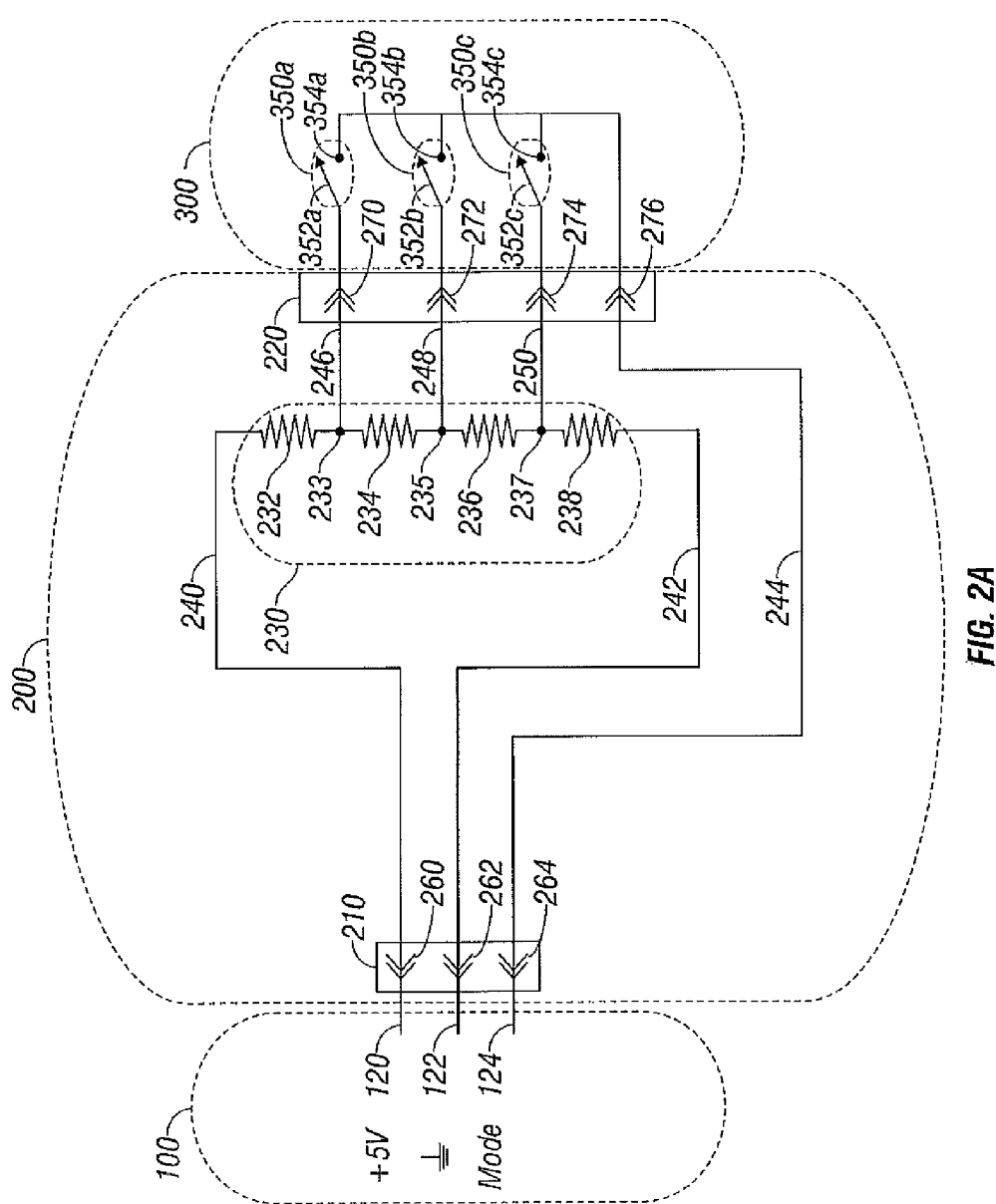
FIG. 2A is a schematic diagram illustrating a connection cable for activating a voltage-controlled electrosurgery generator according to an embodiment of the present disclosure.
Figure 2B:
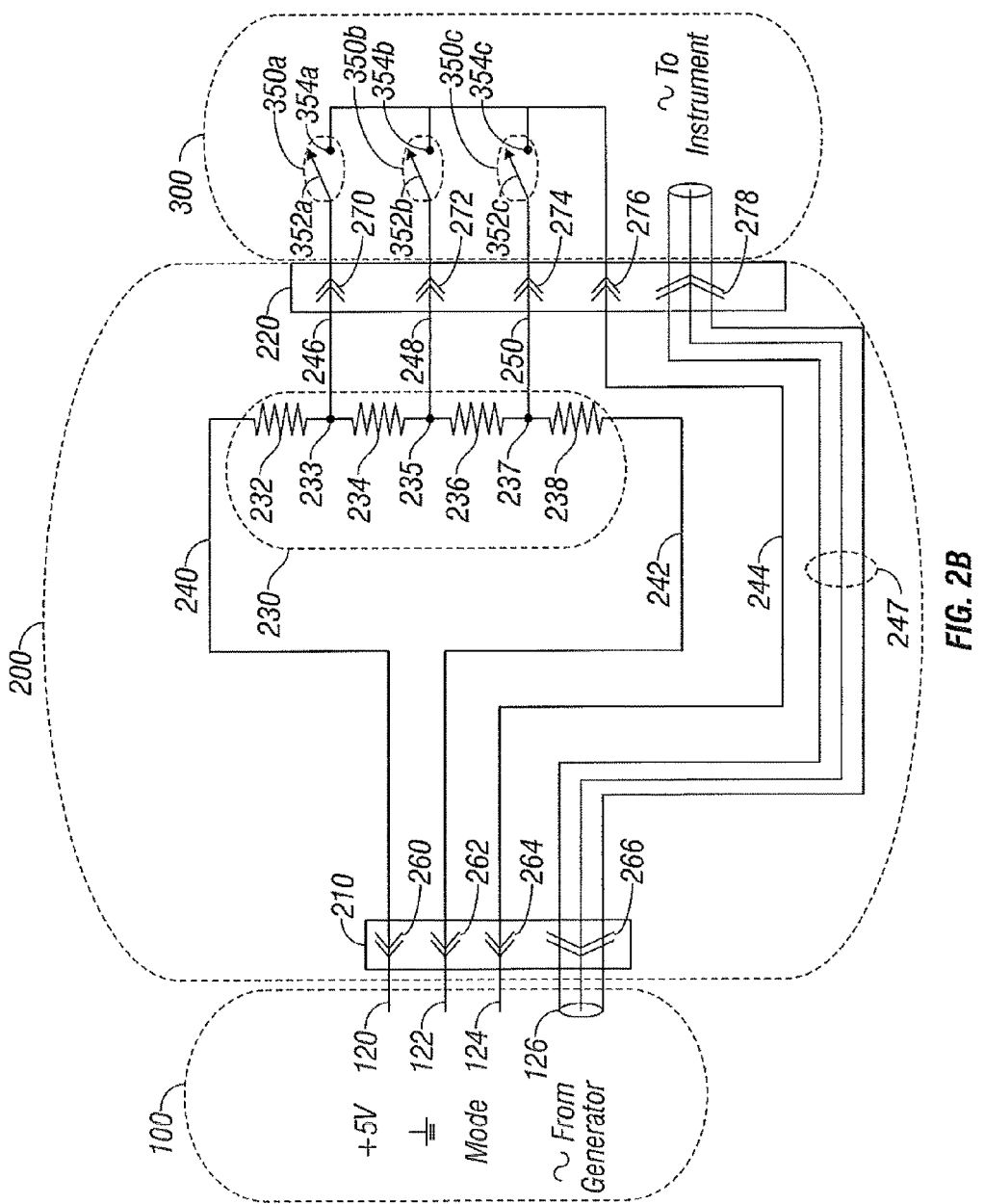
FIG. 2B is a schematic diagram illustrating a connection cable for activating a voltage-controlled electrosurgery generator and for providing an electrosurgical signal to a robotic surgery system according to an embodiment of the present disclosure.

Referring now to FIGS. 2A and 2B, an embodiment of the present disclosure is illustrated wherein electrosurgery generator 100 provides an interface comprising a voltage source 120, a return 122, and a mode input 124. In an embodiment, voltage source 120 provides a substantially constant +5Vdc potential, and return 122 is at ground potential. The electrosurgery generator is configured to generate an electrosurgical signal in response to a control voltage signal applied to mode input 124. As examples only, in response to a +1.67Vdc mode input signal, electrosurgery generator 100 generates a coagulating waveform; in response to a +3.35Vdc mode input a blending waveform is generated; and in response to a +4.18Vdc mode input a cutting waveform is generated. The electrosurgery generator is further configured to determine whether a control voltage input is valid or invalid, to respond only to control voltages recognized as valid, and to ignore all unrecognized (i.e., invalid) voltages. In an embodiment, the electrosurgery generator responds only to mode inputs of +1.67Vdc, +3.35Vdc or +4.18 Vdc; while all other mode input voltages are ignored by the electrosurgery generator. Optionally, mode inputs falling within an accepted tolerance, for example, within +/− 0.10 Vdc of any of the nominal voltages known to be valid, are also recognized, thereby causing a corresponding electrosurgical signal to be generated.

Alternate embodiments are envisioned within the present disclosure, such as an electrosurgery generator configured to provide operator-specified waveforms in response to mode inputs, and/or an electrosurgery generator configured to recognize a fewer or greater number of mode input control voltage values and to generate electrosurgery waveforms in accordance thereto.

Further embodiments are envisioned by the present disclosure wherein other aspects of an electrosurgery generator, such as intensity, are controlled. For example, an electrosurgical generator is configured with an "intensity" input adapted to accept an intensity control voltage. A second voltage divider network comprising a plurality of resistors connected in series is provided wherein at each voltage tap a control voltage is made available which represents a control voltage corresponding to a preset intensity setting of the electrosurgical waveform. Alternatively, the additional voltage taps may come from the first voltage divider network. In use, the electrosurgical generator includes an algorithm, library or other data storage device for storing the most recently selected intensity setting for use in connection with the generation of subsequent electrosurgical signals.

At least one control voltage is derived from voltage source 120 and return 122 by voltage divider network 230, which includes a plurality of resistors connected in series. Voltage source 120 and return 122 are operatively and detachably coupled to voltage divider network 230 by connector 210 via conductors 240 and 242, respectively. In an embodiment, voltage divider network 230 comprises resistors 232, 234, 236, and 238 connected in series and intervening voltage taps 233, 235, and 237.

Voltage divider network 230 may be configured such that, in the event that two or more switches are closed simultaneously, an unrecognized control voltage is provided to the mode input of the electrosurgery generator, which is programmed to ignore unrecognized control voltages.

The robotic surgery system may also include one or more switches 350a, 350b and 350c (hereinafter 350a-c) under control of a surgeon operating the robotic surgical system. For the purposes herein the terms "switch" or "switches" includes electrical actuators, mechanical actuators, electro-mechanical actuators (e.g., rotatable actuators, pivotable actuators, toggle-like actuators, buttons, etc.), optical actuators, or other suitable switches. In an embodiment, switches 350a-c are of a normally open, momentary contact, single pole single throw, type having a first contact 352a, 352b, and 352c, respectively (hereinafter 352a-c), and a second contact 354a, 354b, and 354c, respectively (hereinafter 354a-c). Other embodiments are envisioned wherein the switch 350a-c includes a set of relay contacts, a solid state switch, or equivalent switches as may now or hereafter be known in the art. Each first contact 352a-c of switch 350a-c is detachably and operatively coupled by connector 220 to a conductor electrically connected to a corresponding voltage tap, for example, by conductor 246 to voltage tap 233, conductor 248 to voltage tap 235, and conductor 250 to voltage tap 237. Each second contact 354a-c of switch 350a-c is commonly coupled to conductor 244 of connection cable 200, which is detachably and operatively connected to mode input 124 of electrosurgery generator 100 by connector 210.

In use, a surgeon causes the closure of one of the switches 350a-c to complete a circuit, whereby a corresponding control voltage is applied to mode input 124 of electrosurgery generator 100, which, in turn, responds by generating and outputting a corresponding electrosurgery signal.

Figure 3:
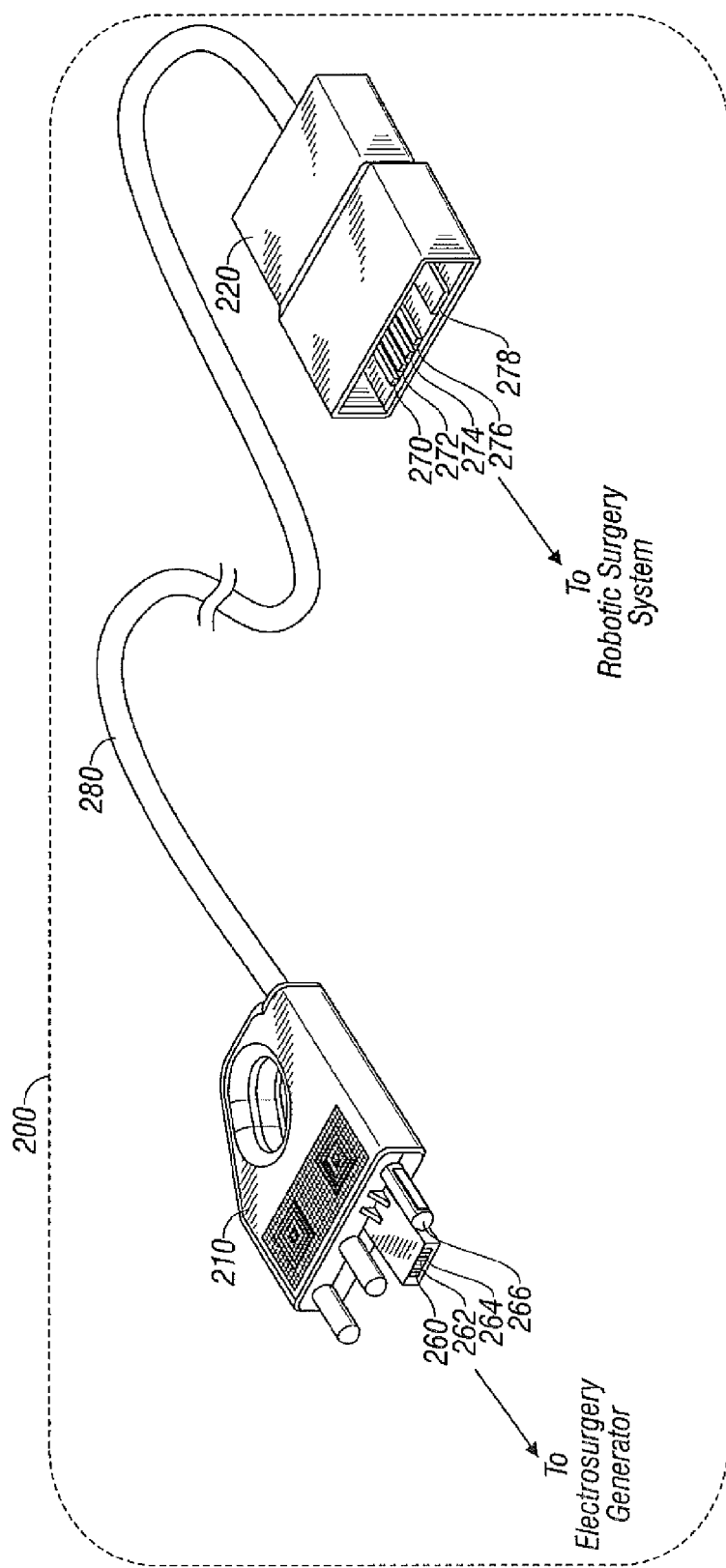
FIG. 3 is a schematic of a connection cable for activating a voltage-controlled electrosurgery generator and for providing an electrosurgical signal to a robotic surgery system in accordance with an embodiment of the present disclosure.

An example embodiment of a connection cable in accordance with the present disclosure is provided with reference to FIG. 3. Connection cable 200 includes a robotic surgery system connector 220 configured to mate with a corresponding connector 224 provided by robotic surgery system as disclosed herein. Cable 280 includes a plurality of independent conductors or wires and electrosurgery generator connector 210 is configured to mate with a corresponding connector 214 provided by a electrosurgery generator as disclosed herein. In an embodiment, cable 280 may be a jacketed cable, a ribbon cable, or other suitable cable.

Robotic surgery system connector 220 may also include contacts 270, 272, and 274 that are disposed in electrical connection with voltage taps 233, 235, and 237, respectively, and contact 276 that is in electrical connection with contact 264 of electrosurgery generator connector 210 via conductor 244. Electrosurgery generator connector 210 may additionally include contacts 260 and 262 that are in electrical connection with voltage divider 230 by conductors 240 and 242, respectively.

Referring now to FIG. 2B, connection cable 200 is optionally configured to deliver the electrosurgical signal from an output 126 of the electrosurgical generator 100 to the robotic surgery system. In an embodiment, electrosurgery generator connector 210 further includes a contact 266, which is in electrical connection via transmission wire 247 of cable 280 to contact 278 of robotic surgery system connector 220.

Variations of the above embodiments are envisioned within the present disclosure. For example, voltage divider 230 may be fully or partially physically supported within connector 210, connector 220, cable 280, or within a separate enclosure independent of (or in combination with) other modules or systems. Further variations of the above-disclosed and other features and functions, or alternatives thereof, may be desirably combined into many other different systems or applications. Various presently unforeseen or unanticipated alternatives, modifications, variations or improvements therein may be subsequently made by those skilled in the art, which are also intended to be encompassed by the following claims.

What is claimed is:

1. A system for performing robotic electrosurgery, the system comprising:
    an electrosurgery generator configured to sense the presence of a control voltage and to produce a corresponding electrosurgical signal in response thereto;
    a robotic surgery system having at least one surgical instrument, the robotic surgery system configured to accept a user input whereby a desired electrosurgery signal is selected, the robotic surgery system further configured to provide a switch closure corresponding to the selected electrosurgery signal; and
    an interface configured to convert the switch closure into a derived control voltage;
    wherein the derived control voltage is capable of activating the electrosurgery generator when a single switch closure is provided by the robotic surgery system, and the derived control voltage is incapable of activating the electrosurgery generator when two or more switch closures are provided by the robotic surgery system.

2. The system according to claim 1 wherein the interface includes a connection cable, which produces at least one derived control voltage corresponding to the switch closure.

3. The system according to claim 2 wherein the connection cable includes a voltage divider having a plurality of resistors connected in series.

4. The system according to claim 1 wherein said interface is further configured to operatively transmit the electrosurgical signal to the at least one surgical instrument.

5. A method for activating a voltage-controlled generator from a controlling device, the method comprising the steps of:
    providing a voltage-controlled generator and a controlling device electrically coupled thereto;
    dividing a reference voltage provided by the voltage-controlled generator into one or more tap voltages;
    receiving at least one control signal originating within the controlling device;
    deriving from among the one or more tap voltages a control voltage in accordance with the received at least one control signal; and
    applying the derived control voltage to a control input of the voltage-controlled generator, wherein the derived control voltage is capable of activating the voltage-controlled generator when a single control signal is received from the controlling device, and the derived control voltage is incapable of activating the voltage-controlled generator when two or more control signals are received from the controlling device.

6. The method according to claim 5, further comprising the step of transmitting the electrosurgical signal to a destination device.

7. The method according to claim 6, wherein the destination device is a surgical instrument.

8. The method according to claim 5, wherein the voltage-controlled generator is an electrosurgery generator.

9. The method according to claim 5, wherein the controlling device is a robotic surgery system.

10. The method according to claim 5, wherein the resultant signal is an electrosurgery signal.

11. A system for performing robotic electrosurgery, the system comprising:
    an electrosurgery generator configured to sense the presence of a control voltage signal and to produce a corresponding electrosurgical signal in response thereto;
    a robotic surgery system having at least one surgical instrument, the robotic surgery system configured to accept at least one user input whereby a desired electrosurgery signal is selected, the robotic surgery system further configured to provide at least one switch closure corresponding to the selected electrosurgery signal; and
    a connection cable adapted to operably couple the electrosurgery generator and the robotic surgery system, and configured to convert the switch closure into a derived control voltage signal; wherein the derived control voltage signal is capable of causing the electrosurgery generator to produce an electrosurgical signal when a single switch closure is provided by, the robotic surgery system, and the derived control voltage signal is incapable of causing the electrosurgery generator to produce an electrosurgical signal when two or more switch closures are provided by the robotic surgery system.

12. The system according to claim 11 wherein the connection cable produces at least one control voltage corresponding to the switch closure.

13. The system according to claim 12 wherein the connection cable includes a voltage divider having a plurality of resistors connected in series.

14. The system according to claim 11 wherein the connection cable is further configured to operatively transmit the electrosurgical signal to the at least one surgical instrument.

* * * * *